US012745971B2

(12) United States Patent
Paul et al.

(10) Patent No.: US 12,745,971 B2
(45) Date of Patent: Sep. 29, 2026

(54) X-RAY IMAGE ANALYSIS SYSTEM, X-RAY IMAGING SYSTEM AND METHOD FOR ANALYSING AN X-RAY IMAGE

(71) Applicant: KONINKLIJKE PHILIPS N.V., Eindhoven (NL)

(72) Inventors: Soubhik Paul, Kolkata (IN); Biswaroop Chakrabarti, Kolkata (IN); Sven Kroenke-Hille, Hamburg (DE); Sudipta Chaudhury, Bangalore (IN); Stewart Matthew Young, Hamburg (DE); Nataly Wieberneit, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 151 days.

(21) Appl. No.: 18/722,635

(22) PCT Filed: Dec. 16, 2022

(86) PCT No.: PCT/EP2022/086254
§ 371 (c)(1),
(2) Date: Jun. 21, 2024

(87) PCT Pub. No.: WO2023/117722
PCT Pub. Date: Jun. 29, 2023

(65) Prior Publication Data
US 2025/0134483 A1 May 1, 2025

(30) Foreign Application Priority Data
Dec. 23, 2021 (EP) .................................... 21217433

(51) Int. Cl.
*A61B 6/00* (2024.01)
*A61B 6/50* (2024.01)
(Continued)

(52) U.S. Cl.
CPC ............ *A61B 6/5217* (2013.01); *A61B 6/505* (2013.01); *A61B 6/5205* (2013.01);
(Continued)

(58) Field of Classification Search
CPC ..... A61B 6/5217; A61B 6/505; A61B 6/5205; G06T 7/0012; G06T 7/70;
(Continued)

(56) References Cited

U.S. PATENT DOCUMENTS

2015/0223941 A1* 8/2015 Lang .................. A61B 17/1778 606/87
2016/0148375 A1* 5/2016 Oh ......................... A61B 5/743 382/131
2020/0211186 A1* 7/2020 Gong ................... A61B 5/0033

FOREIGN PATENT DOCUMENTS

CN 109741316 A * 5/2019
CN 113592834 A 11/2021
WO WO-2017090083 A1 * 6/2017 ............. A61B 5/107
WO WO-2020083764 A1 * 4/2020 ........... G06T 7/0012

OTHER PUBLICATIONS

Namayega "A deep learning algorithm for contour detection in synthetic 2D bi-planar X-ray images of the scapula: towards improved 3D reconstruction of the scapula", University of Cape Town; Aug. 31, 2020; p. 1-77. (Year: 2020).*
(Continued)

*Primary Examiner* — Casey Bryant
*Assistant Examiner* — Mamadou Faye
(74) *Attorney, Agent, or Firm* — Larry Liberchuk

(57) ABSTRACT

The invention relates to an X-ray image analysis system (4) comprising an X-ray image input interface (8) and a computing unit (9). The X-ray image input interface (8) is configured to receive X-ray images (14) taken by an X-ray imaging system (1) comprising an X-ray source (2) and an X-ray detector (3). The computing unit (9) is connected to
(Continued)

the X-ray image input interface (8) and configured to obtain at least one X-ray image (14) from the X-ray image input interface (8) and perform a scapula position detection, including inputting the X-ray image (14) into a trained machine-learning system, running the trained machine-learning system, and obtaining a scapula position. The computing unit (9) is further configured to transmit scapula position information from a scapula position information output interface (10) to a display (5). The invention further relates to an X-ray imaging system (1) comprising an X-ray source (2), an X-ray detector (3), an X-ray image analysis system (4) according to the above description, and the display (5) configured to receive and display the scapula position information as well as to a method for analyzing an X-ray image.

12 Claims, 4 Drawing Sheets

(51) Int. Cl.
*G06T 7/00* (2017.01)
*G06T 7/70* (2017.01)

(52) U.S. Cl.
CPC .............. *G06T 7/0012* (2013.01); *G06T 7/70* (2017.01); *G06T 2207/10116* (2013.01); *G06T 2207/20081* (2013.01); *G06T 2207/20084* (2013.01); *G06T 2207/30008* (2013.01); *G06T 2207/30061* (2013.01)

(58) Field of Classification Search
CPC ........... G06T 2207/10116; G06T 2207/20081; G06T 2207/20084; G06T 2207/30008; G06T 2207/30061; G06T 5/60; G06T 5/94; G06T 2207/10152; G06T 2207/20224; G06T 5/50; G06T 7/33; G06T 7/62; G06T 2207/20128; G06T 2207/30168; G06T 7/11
See application file for complete search history.

(56) References Cited

OTHER PUBLICATIONS

Translation of WO2017/090083 A1 (Year: 2017).*
Translation of CN109741316A; (Year: 2019).*
PCT International Search Report, International application No. PCT/EP2022/086254, May 25, 2023.
Hofmanninger J. et al., "Separation of Target Anatomical Structure and Occlusions in Chest Radiographs", arxiv.org, Cornell University Library, 201 Olin Library Cornell University Ithaca, NY 14853, Feb. 2020, XP081590146.
Vogelsang F. et al., "Detection and Compensation of Rib Structures in Chest Radiographs for Diagnose Assistance", Proceedings of SPIE, IEEE, US, vol. 3338, No. Part 01/02, Feb. 1, 1998 , pp. 774-785, XP001004708.
Yang Z. et al., "Automatic Bone Segmentation and Bone-Cartilage Interface Extraction for the Shoulder Joint from Magnetic Resonance Images", Physics in Medicine and Biology, Institute of Physics Publishing, Bristol GB, vol. 60, No. 4, Jan. 22, 2015, pp. 1441-1459, XP020278929.
Fu Y. et al., "Automatic and Hierarchical Segmentation of the Human Skeleton in CT Images", Physics in Medicine and Biology, Institute of Physics Publishing, Bristol GB, vol. 62, No. 7, Mar. 14, 2017, pp. 2812-2833, XP020315172.
Lian J. et al., A Structure-Aware Relation Network for Thoracic Diseases Detection and Segmentation, IEEE Transactions on Medical Imaging, IEEE, USA, vol. 40, No. 8, Aug. 2021, pp. 2042-2052, XP011867808.
Brosch T. et al., "Foveal Fully Convolutional Nets for Multi-Organ Segmentation", Proceedings of the SPIE, Medical Imaging 2018: Image Processing; vol. 105740U, pp. 198-206, Mar. 2018.
Vock P. et al., "Dual Energy Subtraction: Principles and Clinical Applications", European Journal of Radiology, vol. 72, No. 2, pp. 231-237, Nov. 2009.
Koninklijke Philips N.V., "Philips Bone Suppression Delivering Confidence in Image Interpretation", Feb. 2020. https://www.usa.philips.com/c-dam/b2bhc/master/landing-pages/dynamic-uniquePhilips_Bone_Suppression_product_overview_v5_FINAL.pdf.
Von Berg J. et al., "A Novel Bone Suppression Method That Improves Lung Nodule Detection: Suppressing Dedicated Bone Shadows in Radiographs While Preserving the Remaining Signal", International Journal of Computer Assisted Radiology and Surgery (JCARS), vol. 11, No. 4, pp. 641-655, Apr. 2016.

* cited by examiner

11

12

X-RAY IMAGE ANALYSIS SYSTEM, X-RAY IMAGING SYSTEM AND METHOD FOR ANALYSING AN X-RAY IMAGE

FIELD OF THE INVENTION

The invention relates to an X-ray image analysis system, to an X-ray imaging system with an X-ray image analysis system, and to a method for analyzing an X-ray image.

BACKGROUND OF THE INVENTION

Assessment of chest radiograph quality is an important step in radiological interpretation. Automatic quality checks can provide support during image interpretation, e.g., by alerting the radiologist to the presence of overlapping scapula and lung parenchyma, and enable image reacquisition before the patient has left the imaging room. Scapula position during chest radiography is an important quality parameter, ideally the scapula should have no overlap with the lung parenchyma. If the scapulae overlap with parenchyma within the image, any pathological features present within the peripheral upper zones and pleura may be obscured. For example, there may be difficulty in diagnosing lesions like a small pneumothorax, pleural thickening, loculated effusion, subtle opacifications in peripheral upper lobes in the presence of an overlapping scapula. The radiologist should at least be alerted to such an overlap and if the ambiguity is too high, image reacquisition may be warranted. It is also observed that in certain critical conditions like pneumothorax, the scapula border can be confused with the contracted lung boundary and may lead to a wrong diagnosis. Similar confusion can happen even with other lesions such as nodules present in the lung parenchyma.

WO 2020/083764 discloses a system for analysis of medical images which is configured to determine quality parameter values, wherein the quality parameter values may be based on for example a scapula.

SUMMARY OF THE INVENTION

It is an object of the present invention to provide an X-ray image analysis system that performs an automatic check of an X-ray image and provides information related to the position of the scapula to a radiologist. It is a further object of the present invention to provide an X-ray imaging system with an X-ray image analysis system and a method for analyzing an X-ray image that perform an automatic check of an X-ray image and provide information related to the position of the scapula.

The invention is defined by the independent claims. The dependent claims define advantageous embodiments.

In an aspect of the present invention, an X-ray image analysis system is provided. The X-ray image analysis system comprises an X-ray image input interface and a computing unit. The X-ray image input interface may be integrated in the computing unit and/or may be connected to the computing unit, in particular via a wired or wireless connection.

The X-ray image input interface is configured to receive X-ray images taken by an X-ray imaging system. Said X-ray imaging system comprises an X-ray source and an X-ray detector. In operation, X-ray beams emitted by the X-ray source pass a patient, in particular a chest of the patient, and are recorded by the X-ray detector to generate the X-ray image.

The computing unit is connected to the X-ray image input interface and obtains at least one X-ray image from the X-ray image input interface. Here, the X-ray image input interface may receive the X-ray image directly from the X-ray detector, may receive the X-ray image from a separate image preprocessor or may read an X-ray image file already saved to a memory.

Further, the computing unit performs a scapula position detection. Said scapula position detection makes use of a trained machine learning system. For the training of said machine learning system, training X-ray images, in particular of the chest of the patient, have been provided with annotations, e.g., by a clinician or a radiologist. Said annotations are, in particular, borders of the scapula that have been drawn, e.g., on a separate image or on an extra layer of the image. As usual, the training is performed with a subset of the training X-ray images and corresponding annotations, while the remainder of the training X-ray images and the corresponding annotations are used to evaluate the trained model. The training is stopped when a predetermined criterion is reached, such as to ensure that the model has been trained well enough but not over-trained.

For the scapula position detection, the X-ray image is input into the trained machine-learning system, the trained machine-learning system is run with the X-ray image and a scapula position is obtained as output from the trained machine-learning system. In particular, the scapula position is obtained as an image file comprising the scapula border.

Finally, out of the obtained scapula position, scapula position information is generated. Said scapula position information may be used as a quality parameter to alert a lab technician right after the X-ray image is taken and help him take a decision regarding the quality of the image and the need for a re-take before the patient leaves the X-ray room. The scapula position information can also alert the clinician and prevent wrong diagnosis due to an overlap of the scapula with the lung fields during review of the image, in particular in case of critical conditions like a pneumothorax, where the scapula border can be confused with a contracted lung border. Further, if the scapula position information indicates quality issues, the patient may be recalled. Moreover, the scapula position information may be used to suppress the scapula borders in the X-ray image, if, e.g. a patient recall is not possible or not recommended.

The X-ray image analysis system further comprises a scapula position information output interface. Said scapula position information output interface may be integrated in the computing unit and/or it may be connected to the computing unit, in particular via a wired or wireless connection. The computing unit is configured to transfer the scapula position information to the scapula position information output interface, and the scapula position information output interface is configured to receive the scapula position information from the computing unit. The scapula position information output interface then transmits the scapula position information. In particular, the scapula position information is transmitted to a display where it is displayed and can be used by a user, e.g., a clinician and/or a radiologist.

According to an embodiment, image pre-processing is applied to the X-ray image before inputting it into the trained machine-learning system. Said image pre-processing may include region of interest (ROI) cropping of the X-ray image, and may be performed to extract the region where the scapula is present. These ROI cropped images are used instead of the whole image to reduce unnecessary and/or out of context image information. The image pre-processing may also include a normalization of the image intensity or an adjustment of the histogram. For consistency, the same image pre-processing has been applied to the training X-ray images before training the machine-learning system. With pre-processed X-ray images, the scapula position detection with the trained machine-learning system is further improved. Certain state of the art data augmentation techniques such as rotation, flipping, translation may also be applied to the data during the training to make the model more robust and generic.

According to an embodiment, the machine-learning system is a deep learning system, particularly a deep neural network, and most particularly a fully convolutional neural network, since a fully convolutional neural network is particularly well suited for image analysis. However, other suitable machine-learning systems may be used as well.

According to an embodiment, the scapula position information comprises a scapula border. In particular, said scapula border is provided as an image comprising lines that represent the scapula border. Said scapula border may then be visualized together with the X-ray image. This may help a clinician or a radiologist to assess the influence of the scapula on the X-ray image and in particular on those parts of the X-ray image where the scapula overlaps with the lung field. The position of the scapula border may be of particular importance in scenarios where the scapula border may be confused with underlying pathology or where the scapula is obscuring the clinical appearance of the pathology, e.g., when the scapula is overlapping with a nodule or with a pneumothorax. Further, there may be a button that may be pressed to toggle between displaying and not displaying the scapula border in addition to the X-ray image. Hence, the clinician or radiologist may choose whether or not he wants to see the scapula border and switch between both views to assess details of the X-ray image.

According to an embodiment, the computing unit is further configured to detect lung pathologies. The scapula border is then only transmitted if at least one predetermined lung pathology such as a pneumothorax or a nodule has been detected. Hence, the transmission of the scapula border only occurs if there exists a lung pathology that may be obscured by the scapula border. If such a lung pathology does not exist, there may be no need to transmit the scapula border.

The detection of the lung pathologies may be performed using another trained machine learning system. Said other trained machine learning system may be trained using data augmentation: to start with, annotated X-ray images are used in which the scapula is fully rotated outside of the lung field, i.e., in which there is no overlap between the scapula and the lung field. The annotations have once again be performed, e.g., by a clinician or by a radiologist. For each of these annotated X-ray images, one or more simulated scapulae are sampled. For this, the position for the centroid of the scapula may be randomly chosen and a variety of scapula appearances may be mimicked by randomly scaling, rotating and elastically deforming a reference outline of the scapula. Further, the scapula borders may be blurred and intensities within the scapula borders may be assigned to simulate the presence of a real overlapping bone. Training the other machine learning system with this augmented data will result in a model that can distinguish pathologies from the scapula border.

According to an embodiment, the computing unit is further configured to detect a lung field in the X-ray image and to quantify an overlap of the scapula with the lung field. Then, the scapula position information comprises an overlap quantifier, quantifying the overlap of the scapula with the lung field. Said overlap quantifier may serve as a quality parameter that describes the quality of the X-ray image in terms of the amount of overlap of the scapula with the lung field. Additionally or alternatively, the scapula position information comprises an overlap alert that is issued if the overlap quantifier exceeds a predetermined threshold. When this alert is issued, the clinician or the radiologist immediately knows that a re-take of the X-ray image and/or a patient recall should be considered and/or that the X-ray image shall be assessed with extra care.

According to an embodiment, the computing unit is configured to detect the lung field by recognizing a lung contour by image processing. In particular, borders may be found in the X-ray image and the found border segments may be combined to form the lung contour.

Additionally or alternatively, the lung field may be detected by a derivation of the lung contour from a lung atlas. Said lung atlas may comprise a vast collection of lung X-ray images, both of real ones and of ones that have been generated from a lung model. The lung atlas may also comprise an average lung X-ray image that corresponds to a mean of a plurality of lung X-ray images and a corresponding standard deviation. The X-ray image is then matched to the lung atlas, e.g., by identifying characteristic points and/or characteristic areas in the X-ray image.

Additionally or alternatively, the lung contour is detected using yet another trained machine learning system. Said yet other trained machine learning system has been in particular trained with X-ray images that show the lung and are annotated with the lung contour, wherein the annotation has been performed by a clinician and/or radiologist.

According to an embodiment, the quantification of the overlap comprises summing values of distances from the lung contour of all points on the scapula border that lie within the lung contour. By definition, these distances are negative distances, such that the sum is also a negative number. The smaller the absolute value of the sum of the distances, the smaller the overlap of the scapula with the lung field, and the higher the quality of the X-ray image.

According to an embodiment, the quantification of the overlap comprises computing the quotient of an area of an intersection of the scapula and the lung field over an area of a union of the scapula and the lung field or an area of the lung field. In either case, said quotient quantifies the fraction of the overlap area over a full area, and smaller numbers indicate a higher quality of the X-ray image. Further, a varying inhalation status may be compensated for by evaluating the areas in a rib-cage atlas. Said rib-cage atlas comprises a plurality of X-ray images of the rib-cage, in particular at different levels of inhalation. Rib centerlines may be mutually registered in the rib-cage atlas. Hence, by identifying characteristic points and/or characteristic areas in the X-ray image and in the rib-cage atlas, the areas of which the quotient is computed may be mapped from the X-ray image to the X-ray images in the rib-cage atlas. Then, for each of the images in the rib-cage atlas, the quotient may be computed to obtain the quotient at different levels of inhalation.

According to an embodiment, the quantification of the overlap comprises creating a line segment between two intersection points between the scapula border and the lung contour. Using this line segment, a largest distance of points of the scapula border inside the lung field from the line segment may be computed as the overlap quantifier. Additionally or alternatively, a diameter of a largest circle that can be fitted inside an area bound by the line segment and the scapula border inside the lung field may be computed as the overlap quantifier. And additionally or alternatively, a ratio of areas of two segments of the scapula on both sides of the line segment may be computed as the overlap quantifier. Either of these overlap quantifiers is a measure for the amount of the scapula overlapping with the lung field and is therefore a measure for the quality of the X-ray image.

According to an embodiment, an affine transformation between the scapula border and a reference scapula border is computed. To do so, the scapula border may be registered to a reference scapula border in an atlas, allowing for individual differences. The affine transformation may map the scapula border to the reference scapula border and the eigenvalues and eigenvectors of this affine transformation may be used as a surrogate for the shape and orientation of the scapular shadow. Hence, the scapula position information comprises the eigenvalues and eigenvectors of the affine transformation. Such an assessment of the orientation of the scapula is beneficial for the following reason: the impact of the overlap of the scapula and the lung field on the clinical interpretation may be different for two X-ray images where the area of overlap is equivalent, but the orientation of the scapula differs. In particular, an atypical orientation may lead to diagnostic difficulty. However, such an atypical orientation is quantified by the eigenvalues and eigenvectors of the affine transformation, informing the clinician and/or radiologist about the atypical orientation.

According to an embodiment, the effects of the scapula are suppressed in the X-ray image to generate an improved X-ray image. Such suppression of the effects of the scapula are of particular importance when there is an overlap of the scapula with the lung field. It is further important in cases where a new X-ray image where the scapula does not overlap the lung field should not be taken to limit the amount of radiation applied to the patient and/or where the new X-ray image cannot be taken because the patient has already left or it is difficult for the patient to stand in correct posture during the radiograph, e.g., in the case of ailing patients.

One option to perform said suppression of the scapula is by image processing, in particular by subtracting the scapula border that has been detected.

Another option to perform the suppression of the scapula is by dual energy subtraction: the scapula has different characteristics with respect to each of the X-ray energies as compared to the lung parenchyma. Hence, by choosing an appropriate linear combination of the two X-ray images with different X-ray energies, the scapula may be suppressed.

Yet another option to perform the suppression of the scapula is to calculate the scapula attenuation using a chest radiograph atlas and subsequently subtracting said calculated scapula attenuation. To do so, the scapula border may be registered to a reference scapula border through an affine transformation. Further, an atlas of chest radiographs with representations of extreme rotations of the scapula around vertical and horizontal axes may be used for reference attenuations due to scapulae. The angles of these rotations may be determined by interpolation between said extremes, and using said angles, the attenuation due to the scapula at each pixel within the boundary of the scapula may be computed and subtracted from the X-ray image. Said subtraction provides an improved suppression of scapula effects since attenuation through the scapula varies as the scapula bone has considerable variation in thickness throughout its extent: while the body is a thin plate, the lateral border, the spine, and acromion and coracoid processes and the glenoid are thicker.

As a result, the scapula position information comprises the improved X-ray image, which may, e.g., be displayed to a clinician and/or radiologist.

In another aspect of the present invention, an X-ray imaging system comprising an X-ray source, an X-ray detector, an X-ray image analysis system according to the above description, and the display is provided. The display is configured to receive and display the scapula position information. Hence, clinicians and/or radiologists are provided with information regarding the overlap of the scapula with the lung field and may take this into account when assessing the X-ray image. Further advantages are given in the above description.

In yet another aspect of the present invention, a method for analyzing an X-ray image is provided. According to the method, at least one X-ray image taken by an X-ray imaging system comprising an X-ray source and an X-ray detector is obtained. Then, a scapula position detection is performed, including inputting the X-ray image into a trained machine-learning system, running the trained machine-learning system, and obtaining a scapula position. Finally, the scapula position information is generated and transmitted from an output to a display. Using said scapula position information, a clinician and/or a radiologist are provided with information regarding the overlap of the scapula with the lung field and may take this into account when assessing the X-ray image. Further advantages are given in the above description.

It shall be understood that a preferred embodiment of the invention can also be any combination of the dependent claims with the respective independent claim.

These and other aspects of the invention will be apparent from and elucidated with reference to the embodiments described hereinafter.

BRIEF DESCRIPTION OF THE DRAWINGS

In the following, preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
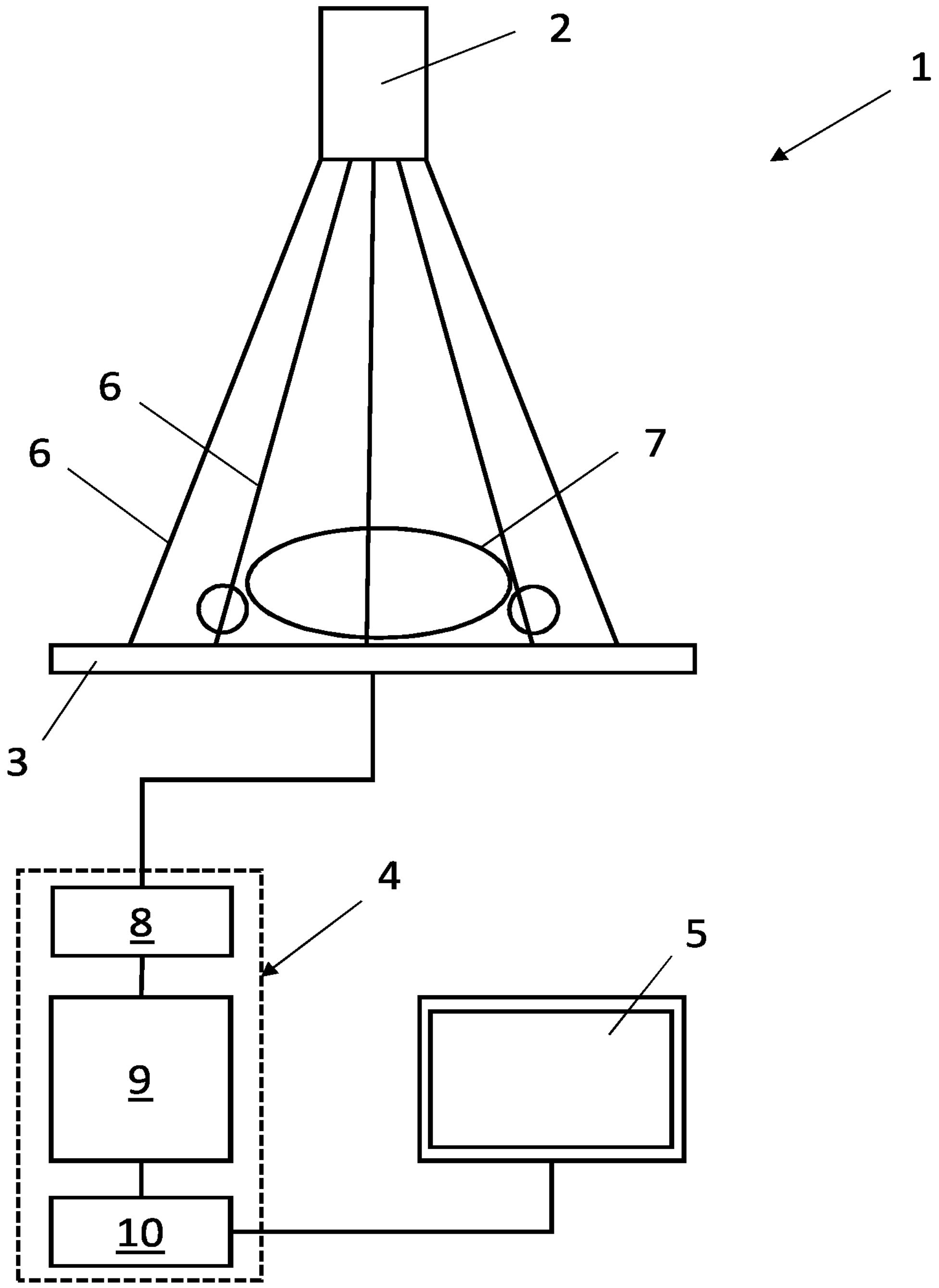
FIG. 1 shows a schematic view of an embodiment of an X-ray imaging system.

FIG. 1 shows a schematic view of an embodiment of an X-ray imaging system 1. The X-ray imaging system 1 comprises an X-ray source 2, an X-ray detector 3, an X-ray image analysis system 4, and a display 5.

The X-ray source 2 is adapted to emit X-ray beams 6, and the X-ray detector 3 is adapted to detect said X-ray beams 6. A patient's chest 7 between the X-ray source 2 and the X-ray detector 3 will cause attenuation of the X-ray beams 6, which will be detected by the X-ray detector 3.

The X-ray detector 3 is connected to an X-ray image input interface 8 of the X-ray image analysis system 4. Said connection may be a wired or a wireless connection. A computing unit 9 of the X-ray image analysis system 4 obtains an X-ray image from the X-ray detector 3 via the X-ray image input interface 8.

The computing unit 9 is configured to perform a scapula detection, including inputting the X-ray image into a trained machine-learning system, running the trained machine-learning system and obtaining a scapula position. Using said scapula position, a scapula position information is generated.

The scapula position information is then transferred to a scapula position information output interface 10, from where it is transmitted to the display 5.

On the display 5, lab technicians, clinicians and/or radiologists may see the scapula position information. Said scapula position information may then be used as a quality parameter to alert the lab technician right after the x-ray is taken and help him take a decision regarding the quality of the image and the need for a re-take before the patient leaves the X-ray room. It may also be used to alert the clinician and prevent wrong diagnosis due to an overlap of the scapula with the lung fields, in particular in case of critical conditions like a pneumothorax, where the scapula border can be confused with a contracted lung border. Further, if the scapula position information indicates quality issues, the patient may be recalled. Moreover, the scapula position information may be used to suppress the scapula borders in the X-ray image, if, e.g. a patient recall is not possible or not recommended.

Figure 2A:
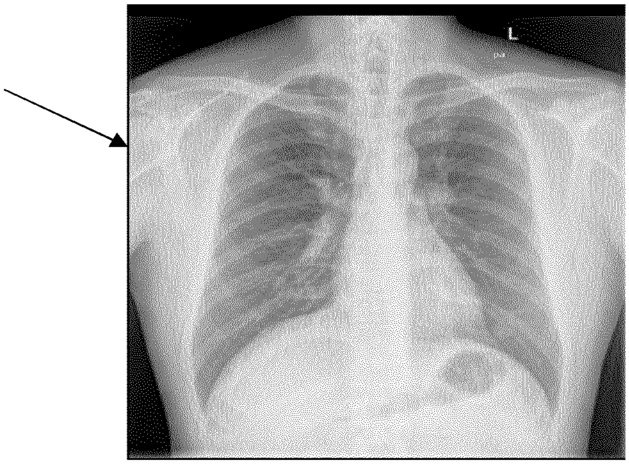
FIGS. 2*a* and 2*b* show an X-ray image and an annotation to the X-ray image.
Figure 2B:
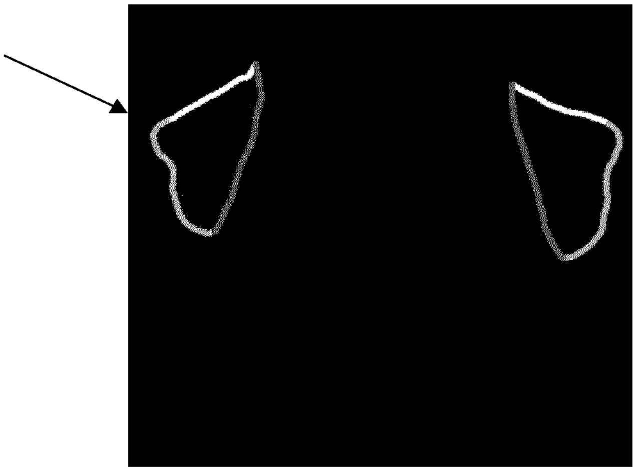

For the training of said machine learning system, training X-ray images, in particular of the chest of the patient, have been provided with annotations, e.g., by a clinician or a radiologist. An example of a training X-ray image 11 is shown in FIG. 2*a* and the corresponding annotations 12 are shown in FIG. 2*b*. Said annotations 12 are borders of the scapula that have been drawn on a separate image or on an extra layer of the image. As usual, the training is performed with a subset of the training X-ray images 11 and the corresponding annotations 12, and the remainder of the training X-ray images 11 and corresponding annotations 12 is used to evaluate the trained model. The training is then stopped when a predetermined criterion is reached, such as to ensure that the model has been trained well enough but not over-trained.

Figure 3:
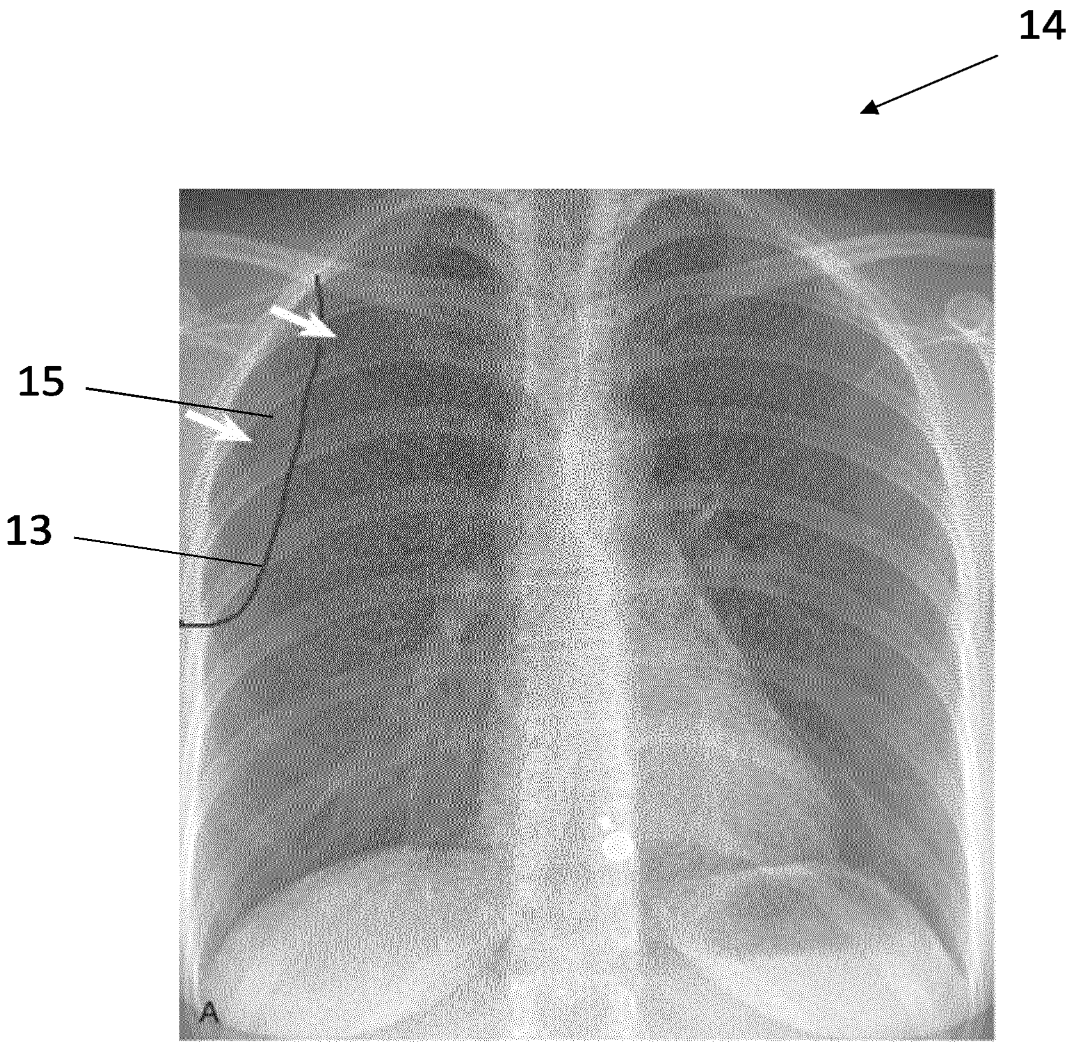
FIG. 3 shows a processed X-ray image.

The scapula position information may comprise a scapula border 13, as shown as a black line in an X-ray image 14 in FIG. 3. Also shown in FIG. 3 and barely visible is a pneumothorax as an example for a lung pathology 15. This is indicated by the white arrows. Since the scapula border 13 is shown in the X-ray image 14, it is less likely that the pneumothorax 15 is not recognized by the clinician and/or radiologist because it is obscured by the scapula border 13.

Figure 4:
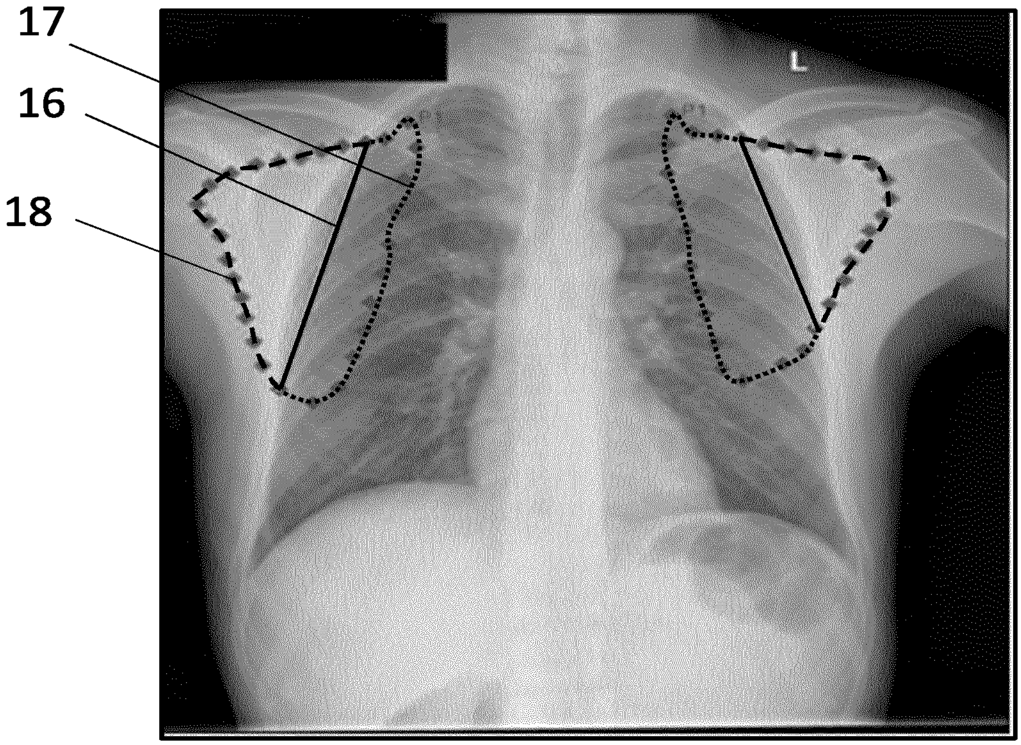
FIG. 4 shows another processed X-ray image.

Finally, FIG. 4 shows an example of a quantification of the overlap of a scapula with a lung field. For this, a line segment 16 (solid line) has been created between two intersection points between the scapula border and the lung contour for each of the scapulae. As one option, a largest distance of points of the scapula border inside the lung field 17 (dotted line) from the line segment may be computed to obtain an overlap quantifier. As another option, a diameter of a largest circle that can be fitted inside an area bound by the line segment 16 and the scapular border inside the lung field 17 may be computed to obtain the overlap quantifier. And as yet another option, a ratio of areas of two segments of the scapula on both sides of the line segment 16, i.e., a ratio of an area bound by the line segment 16 and the scapular border inside the lung field 17 to an area bound by the line segment 16 and the scapular border outside the lung field 18 (dashed line) may be computed to obtain the overlap quantifier. In each case, the overlap quantifier is an indicator of image quality, and a bad image quality may lead to a re-take of the X-ray image, to a suppression of the effects of the scapula and/or to the clinician and/or radiologist paying more attention to possible effects of the scapula.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. Measures recited in mutually different dependent claims may be advantageously combined. Any reference signs in the claims should not be construed as limiting the scope.

LIST OF REFERENCE SIGNS

1 X-ray imaging system
2 X-ray source
3 X-ray detector
4 X-ray image analysis system
5 Display
6 X-ray beam
7 Patient's chest
8 X-ray image input interface
9 Computing unit
10 Scapula position information output interface
11 Training X-ray image
12 Annotation
13 Scapula border
14 X-ray image
15 Lung pathology
16 Line segment
17 Scapular border inside the lung field
18 Scapular border outside the lung field

The invention claimed is:

1. An X-ray image analysis system, comprising:

an X-ray image input interface configured to receive X-ray images taken by an X-ray imaging system comprising an X-ray source and an X-ray detector; and a processor connected to the X-ray image input interface and configured to:

obtain at least one X-ray image from the X-ray image input interface;

perform a scapula position detection, including inputting the X-ray image into a trained machine-learning system, running the trained machine-learning system, and obtaining a scapula position;

detect at least one lung pathology using another trained machine learning system; and generate scapula position information; and a scapula position information output interface configured to receive the scapula position information from the processor and transmit the scapula position information to a display only if the at least one lung pathology has been detected.

2. The X-ray image analysis system according to claim 1, wherein image pre-processing is applied to the X-ray image before inputting into the trained machine-learning system.

3. The X-ray image analysis system according to claim 1, wherein the machine-learning system is a deep learning system comprising a fully convolutional neural network.

4. The X-ray image analysis system according to claim 1, wherein the scapula position information comprises a scapula border.

5. The X-ray image analysis system according to claim 1, wherein the processor is further configured to detect a lung field in the X-ray image and to quantify an overlap of the scapula with the lung field, and the scapula position information comprises an overlap quantifier, quantifying the overlap of the scapula with the lung field and/or an overlap alert that is issued if the overlap quantifier exceeds a predetermined threshold.

6. The X-ray image analysis system according to claim 5, wherein the processor is configured to detect the lung field using at least one of:

recognition of a lung contour by image processing;

derivation of the lung contour from a lung atlas; and detection of the lung contour using yet another trained machine learning system.

7. The X-ray image analysis system according to claim 5, wherein the quantification of the overlap comprises summing values of distances from the lung contour of all points on the scapula border that lie within the lung contour.

8. The X-ray image analysis system according to claim 5, wherein the quantification of the overlap comprises computing the quotient of an area of an intersection of the scapula and the lung field over an area of a union of the scapula and the lung field or an area of the lung field, wherein a varying inhalation status is compensated for by evaluating the areas in a rib-cage atlas.

9. The X-ray image analysis system according to claim 5, wherein the quantification of the overlap comprises creating a line segment between two intersection points between the scapula border and the lung contour, and computing at least one of:

a largest distance of points of the scapula border inside the lung field from the line segment;

a diameter of a largest circle that can be fitted inside an area bound by the line segment and the scapular border inside the lung field; and a ratio of areas of two segments of the scapula on both sides of the line segment.

10. The X-ray image analysis system according to claim 1, wherein an affine transformation between the scapula border and a reference scapula border is computed, and the scapula position information comprises eigenvalues and eigenvectors of the affine transformation.

11. The X-ray image analysis system according to claim 1, wherein effects of the scapula are suppressed in the X-ray image to generate an improved X-ray image by at least one of:

image processing;

dual energy subtraction;

calculation of scapula attenuation using a chest radiograph atlas and subtraction of the calculated scapula attenuation; and the scapula position information comprises the improved X-ray image.

12. A method for analyzing an X-ray image, comprising obtaining at least one X-ray image taken by an X-ray imaging system comprising an X-ray source and an X-ray detector;

performing a scapula position detection, including inputting the X-ray image into a trained machine-learning system, running the trained machine-learning system, and obtaining a scapula position;

detecting at least one lung pathology using another trained machine learning system;

generating scapula position information; and transferring the scapula position information from a scapula position information output interface to a display only if the at least one lung pathology has been detected.

* * * * *